United States Patent [19]

Pinsak et al.

[11] Patent Number: 4,692,748
[45] Date of Patent: Sep. 8, 1987

[54] APPARATUS FOR DETERRING THUMBSUCKING

[76] Inventors: George F. Pinsak, 1102 E. Franklin St., Monroe, N.C. 28110; Henry H. Morton, Jr., 100 Covington St., Wadesboro, N.C. 28170

[21] Appl. No.: 887,863

[22] Filed: Jul. 18, 1986

[51] Int. Cl.⁴ .............................................. G08B 21/00
[52] U.S. Cl. .................................. 340/573; 200/61.04; 200/DIG. 2; 340/604
[58] Field of Search .............................. 340/573, 604; 200/61.04, DIG. 2

[56] References Cited

U.S. PATENT DOCUMENTS 4,178,589 12/1979 Nunn et al. ......................... 340/573
4,613,139 9/1986 Robinson, II ................ 200/DIG. 2

Primary Examiner—Glen R. Swann, III
Attorney, Agent, or Firm—Shefte, Pinckney & Sawyer

[57] ABSTRACT

A glove apparatus for deterring thumbsucking, including a glove body to which is affixed a battery-operated electrical alarm arrangement. The alarm arrangement includes a module containing a battery, an alarm device, and an electrical contact mounted in the wristband of the glove body for surface contact by the electrical contact with the user's wrist. An electrical wire lead extending through the glove body connects the module electrically with another electrical contact insulatively attached to the outward surface of the thumb portion of the glove body to be exposed outwardly without being in surface or other electrical contact with the user's thumb. When the user inserts the thumb into the mouth, a continuous electrical circuit is completed through the alarm arrangement and through the user's body to enable the battery to activate the alarm device to sound an audible alarm alerting the user to remove the thumb from the mouth.

10 Claims, 1 Drawing Figure

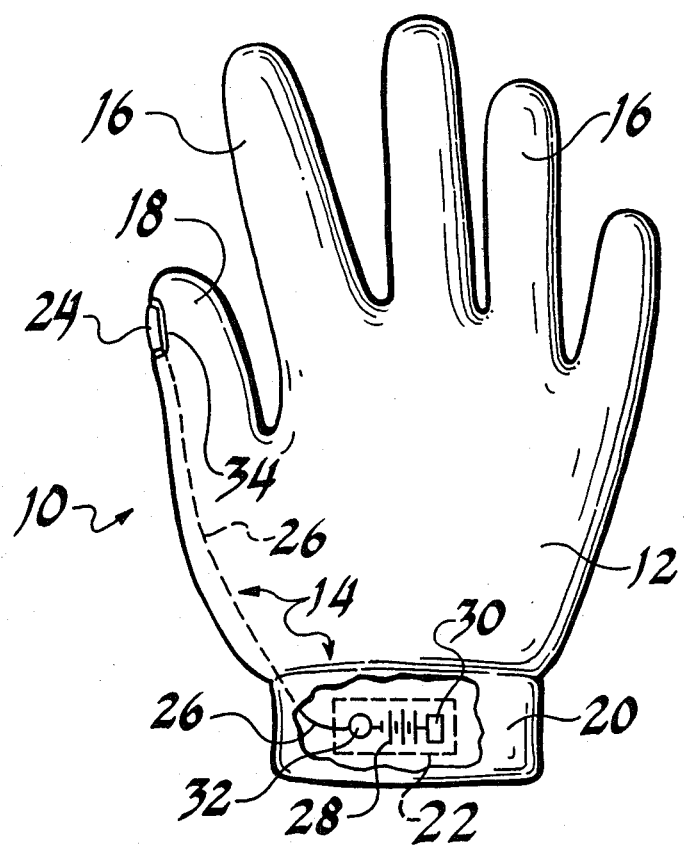

APPARATUS FOR DETERRING THUMBSUCKING

BACKGROUND OF THE INVENTION

It is a longstanding common phenomenon that many children develop the habit of sucking one thumb or finger as an apparent means of pacification. The habit typically begins in infancy and usually is outgrown during early childhood development, although some children continue the practice into adolescence. The cause of this habit is unknown, but regardless of the cause most child development authorities agree that the habit can lead to dental deformities and other similar medical problems if not corrected during early childhood development. Over the years, parents, physicians and other childhood development authorities have proposed and utilized various techniques for deterring children from this practice but no technique has yet been developed which provides continuing reliable results. Close supervision of a child together with repetitive admonishment to avoid the practice seem to provide the greatest degree of success during a child's waking hours. However, experience has generally proven that children nevertheless tend to return to the practice during sleeping hours.

SUMMARY OF THE INVENTION

It is accordingly a principal object of the present invention to provide a safe and reliable apparatus for deterring a child or any other person from the practice of thumbsucking or fingersucking, which may be utilized both during waking and sleeping hours.

Briefly described, the apparatus of the present invention basically includes two electrical contacts with a circuit arrangement electrically connecting the contacts for potential electrical current flow therebetween, with a course of electrical current such as a battery and a suitable alarm mechanism electrically associated with the circuit arrangement for activation by electrical current flow through the circuit arrangement. A suitable arrangement is provided for attaching one contact in electrical contact with the person's skin and for attaching the second contact to one of the person's digits in electrically insulated relation therefrom and exposed outwardly thereof. In this manner, the apparatus is adapted for completing a continuous electrical circuit through the circuit arrangement and through the body of the person when the digit is inserted in the person's mouth in electrical contact therewith for permitting flow of electrical current from the source through the circuit arrangement to activate the alarm mechanism to alert the person to remove the digit from the mouth.

In the preferred embodiment, the apparatus is embodied in a glove adapted to be worn on the person's hand, the first-mentioned electrical contact being affixed to the glove body for electrical contact with the person's skin during wearing and the second-mentioned electrical contact being affixed to the glove body for exposure outwardly of the person's thumb in electrically insulated relation therefrom. The circuit arrangement extends through the glove between the contacts with the battery or other current source and the alarm mechanism also attached to the glove body in electrical association with the circuit arrangement. Preferably, the alarm mechanism is adapted for producing an audible signal when activated. It is also preferred that the glove include a distinct thumb portion on which the second contact is supported and a cuff portion for wearing about the person's wrist to which is attached a module containing the first electrical contact, the battery and the alarm mechanism. The battery is of the type providing a low voltage source of electric current to avoid any risk of electrical shock to the wearer.

BRIEF DESCRIPTION OF THE DRAWING

The accompanying drawing is a schematic plan view of the apparatus of the present invention as preferably embodied in a hand glove.

DESCRIPTION OF THE PREFERRED EMBODIMENT

Referring now to the accompanying drawing, a glove apparatus according to the preferred embodiment of the present invention is indicated generally at 10 and basically includes a glove body, indicated generally at 12, to which is attached an electrical alarm arrangement, indicated generally at 14.

The glove body 12 is of a generally conventional glove construction adapted to be worn on the hand and including individual finger pockets 16 and a distinct thumb pocket 18 with an elasticized or similar wrist band 20 or other cuff portion. For sake of comfort and safety, the glove body 12 should preferably be constructed of a hypo-allergenic non-toxic material such as cotton fabric and should be adapted to closely conform to the user's hand. The wrist band 20 and the thumb pocket 18 may conveniently be of a double-ply construction for receipt and attachment therewith of the alarm arrangement 14 as hereinafter described.

The alarm arrangement 14 basically includes a battery-operated alarm module, schematically represented at 22, affixed to the glove body 12 within the wristband 20 and electrically connected in series with an electrical contact 24 attached to the exterior surface of the thumb pocket 18 through a suitable electrical circuit arrangement 26, which may be simply an insulated electrical wire lead, extending between the module 22 and the contact 24 through the thumb pocket and wristband 18, 20, to establish the potential for electrical current flow between the module 22 and the electrical contact 24. The module 22 includes a low voltage battery 28, which may be of any appropriate conventional type such as a conventional wristwatch battery, electrically connected in series with another electrical contact 30 and a conventional audible alarm device, representatively indicated at 32, which also may be of any appropriate conventional construction such as a conventional wristwatch beeper device. The electrical contact 30 is mounted at one side surface of the module 22 and is exposed through the inwardly-facing surface of the wristband 20 to be in direct surface contact with the wrist of the wearer when the glove apparatus 10 is worn to establish electrical contact with the wearer's wrist. The electrical contact 24 is shielded on its inwardly-facing side by a suitable electrically insulative material 34 to maintain the contact 24 out of electrical surface contact with the wearer's thumb. Of course, as those persons skilled in the art will recognize, the contact 24 may be attached to any one of the finger pockets 16 or an individual contact 24 may be attached to each of the finger and thumb pockets 16, 18 to operate to deter sucking of either the thumb or any finger.

The operation of the glove apparatus 10 will thus be understood. As is well known, the human body can act as a relatively good conductor of electricity. Accordingly, when the glove apparatus 10 is worn, the contact of the electrical contact 30 with the wrist of the wearer establishes the potential for electrical current flow through the components of the alarm arrangement 14 and through the wearer's body. Accordingly, during ordinary wearing of the glove apparatus 10 with the thumb portion 18 out of surface contact with any other part of the wearer's body, no electrical circuit is created through the alarm arrangement 14 since the insulation 34 prevents electrical surface contact between the wearer's thumb and the electrical contact 24 and, in turn, electrical current is not permitted to flow from the battery 28 and the alarm device 32 is deactivated. On the other hand, whenever the electrical contact 24 is brought into electrical contact with any other part of the wearer's body, such as would occur if the wearer inserts the thumb into the wearer's mouth, a continuous electrical circuit is immediately completed through the alarm arrangement 14 and through the wearer's body, thereby permitting electrical current flow from the battery 28 through the resultant circuit to immediately actuate the alarm device 32 to sound an audible signal to alert the wearer to remove the thumb from the mouth. Although as will be understood, such an electrical circuit will be potentially created any time the electrical contact 24 touches any part of the wearer's body, the moist conditions which prevail in the human mouth are especially conductive to the completion of an electrical circuit as described and therefore provides reliable operation of the glove apparatus 10. Importantly, the low voltage potential of the battery 28 essentially eliminates any risk that electrical shock may occur to the wearer when an electrical circuit is completed in the described manner.

The present apparatus thus provides several significant advantages over conventional techniques for deterring children from thumbsucking. Most importantly, the glove apparatus 10 operates automatically in the described manner and therefore does not require close parental supervision. Accordingly, the glove apparatus 10 is of particular usefulness while a child is sleeping in that the apparatus is operative to automatically activate the alarm device 32 each time the child attempts, either consciously or subconsciously, to insert the thumb into the mouth. At the same time, the glove apparatus 10 is comfortable for the child to wear and does not significantly restrict or impair the child's activities so that the apparatus may be utilized during both sleeping and waking hours if desired. As a result, the present glove apparatus 10 may be employed either as the sole deterrent to a child's thumbsucking or may be utilized at selective times such as sleeping hours as an adjunct deterrent in conjunction with conventional deterrent techniques, such as close parental supervision, which may be utilized during a child's waking hours. The low voltage power source provided by the battery 28 provides the glove apparatus 10 with a reasonably long life while also providing optimal safety.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. Apparatus for deterring a person from sucking a digit of the hand, said apparatus comprising a first electrical contact, a second electrical contact, circuit means electrically connecting said first and second electrical contacts for potential electrical current flow therebetween, a source of electrical current electrically associated with said circuit means for supplying electrical current thereto, alarm means electrically associated with said circuit means for activation by electrical current flow through said circuit means, and means for attaching said first contact in electrical contact with the person's skin and for attaching said second contact to one digit of the person's hand in electrically insulated relation therefrom and exposed outwardly thereof for completing a continuous electrical circuit through said circuit means and through the body of the person when the digit is inserted in the person's mouth in electrical contact therewith for permitting flow of electrical current from said source through said circuit means to activate said alarm means to alert the person to remove the digit from the mouth.

2. Apparatus for deterring a person from sucking a digit of the hand according to claim 1 and characterized further in that said electric current source is a low voltage battery.

3. Apparatus for deterring a person from sucking a digit of the hand according to claim 1 and characterized further in that said alarm means includes means for sounding an audible signal.

4. Apparatus for deterring a person from sucking a digit of the hand according to claim 1 and characterized further in that said attaching means includes glove means for wearing on the person's hand.

5. Glove apparatus for deterring a person from thumbsucking, said glove apparatus comprising a glove body adapted to be worn on the person's hand, a first electrical contact affixed to said glove body for electrical contact with the person's skin, a second electrical contact affixed to said glove body for exposure outwardly of the person's thumb in electrically insulated relation therefrom, circuit means electrically connecting said first and second electrical contacts for potential electrical current flow therebetween, battery means attached to said glove body in electrical association with said circuit means for supplying electrical current thereto, and alarm means attached to said glove body in electrical association with said circuit means for activation of an audible signal by electrical current flow through said circuit means, said first and second electrical contacts being adapted to complete a continuous electrical circuit through said circuit means and through the body of the person when the thumb is inserted in the person's mouth in electrical contact therewith for permitting flow of electrical current from said battery means through said circuit means to activate said alarm means to alert the person to remove the thumb from the mouth.

6. Glove apparatus for deterring a person from thumbsucking according to claim 5 and characterized further in that said battery means is arranged to provide a source of low voltage electric current to avoid risk of electrical shock to the person.

7. Glove apparatus for deterring a person from thumbsucking according to claim 5 and characterized further in that said first electrical contact, said battery means and said alarm means are mounted together as a module attached to said glove body.

8. Glove apparatus for deterring a person from thumbsucking according to claim 7 and characterized further in that said glove body includes a cuff portion, said module being attached to said cuff portion for contact of said first electrical contact with the person's wrist.

9. Glove apparatus for deterring a person from thumbsucking according to claim 8 and characterized further in that said glove body includes a thumb portion, said second electrical contact being attached to said thumb portion and exposed outwardly therefrom.

10. Glove apparatus for deterring a person from thumbsucking according to claim 9 and characterized further in that said battery means is arranged to provide a source of low voltage electric current to avoid risk of electrical shock to the person.

* * * * *

UNITED STATES PATENT OFFICE
CERTIFICATE OF CORRECTION

Patent No. 4,692,748     Dated September 8, 1987

Inventor(s) George F. Pinsak and Henry H. Morton, Jr.

It is certified that error appears in the above-identified patent and that said Letters Patent are hereby corrected as shown below:

Col. 2, Line 31, delete "therewith" and insert therefor — therewithin — .

Col. 3, Line 15, between "electrical" and "contact" insert — surface — .

Signed and Sealed this

Nineteenth Day of July, 1988

Attest:

DONALD J. QUIGG

*Attesting Officer*     *Commissioner of Patents and Trademarks*